US006718833B2

(12) United States Patent
Xie et al.

(10) Patent No.: US 6,718,833 B2
(45) Date of Patent: Apr. 13, 2004

(54) MULTIAXIAL HIGH CYCLE FATIGUE TEST SYSTEM (75) Inventors: Ming Xie, Beavercreek, OH (US); Som R. Soni, Beavercreek, OH (US); Charles J. Cross, Centerville, OH (US); Gary E. Terborg, Englewood, OH (US)

(73) Assignees: AdTech Systems Research, Inc., Beavercreek, OH (US); The United States of America as represented by the Secretary of the Air Force, Washington, DC (US)

( * ) Notice: Subject to any disclaimer, the term of this patent is extended or adjusted under 35 U.S.C. 154(b) by 108 days.

(21) Appl. No.: 10/085,916

(22) Filed: Feb. 28, 2002

(65) Prior Publication Data

US 2002/0162400 A1 Nov. 7, 2002

Related U.S. Application Data (60) Provisional application No. 60/273,134, filed on Mar. 5, 2001.

(51) Int. Cl.$^7$ .................................................. G01N 3/32
(52) U.S. Cl. ............................ 73/812; 73/789; 73/794; 73/798; 73/814; 73/816
(58) Field of Search .......................... 73/789, 794, 798, 73/808, 812, 816, 810, 814

(56) References Cited

U.S. PATENT DOCUMENTS

| 3,603,143 | A |   | 9/1971  | Detert et al. |
| 3,696,512 | A |   | 10/1972 | von Marinelle et al. |
| 4,607,531 | A |   | 8/1986  | Meline et al. |
| 4,748,854 | A |   | 6/1988  | Rao |
| 4,802,365 | A | * | 2/1989  | Sallberg et al. ............. 73/808 |
| 4,869,111 | A |   | 9/1989  | Ohya et al. |
| 4,875,375 | A |   | 10/1989 | Wa et al. |
| 5,913,246 | A | * | 6/1999  | Simonelli et al. ............ 73/808 |
| 6,023,980 | A |   | 2/2000  | Owen et al. |
| 6,250,166 | B1| * | 6/2001  | Dingwell et al. ............ 73/810 |

* cited by examiner

Primary Examiner—Edward Lefkowitz
Assistant Examiner—Jermaine Jenkins
(74) Attorney, Agent, or Firm—Bernard E. Franz

(57) ABSTRACT

A multiaxial high cycle fatigue test system for testing bending, torsion, and tension of a test unit, comprises servo-hydraulic components, including a hydraulic service manifold, two small high frequency actuators along a first axis, and one large main actuator along a second axis The large main actuator is used to apply a radial centrifugal force, and the two small actuators are used to apply vibratory loading; the two small side actuators being offset independently of each other, to enable the machine to apply both bending loads and torque to the test unit.

The test unit is subjected to torsion loading when the traverse actuators move in phase, that is when both actuators move either in or out at the same time. The test unit is subjected to bending loading when the actuators move out-of-phase, that is one actuator moves in when the other moves out or vice-versa.

8 Claims, 8 Drawing Sheets

Bending (First mode)    Torsion (Third mode)

Bending and torsion of gas turbine fan blade

Bending (First mode)   Torsion (Third mode)

Figure 1.1 Bending and torsion of gas turbine fan blade

Figure 2.1 Schematic of biaxial loading machine

Figure 2.2 Photograph of biaxial loading machine

Figure 2.3 Blade gripping system for biaxial machine

Figure 2.4 Photograph of biaxial loading of GE F110 fan blade

Figure 3.1 Transverse Loading in the Multiaxial Machine

Figure 3.2 Torsion loading

Figure 3.3 Bending loading

Figure 3.4 Three dimensional model of multiaxial loading mechanism

Figure 3.5 Transverse Loading of Blade

Figure 3.6 Photograph of multiaxial loading setup

Figure 3.7 Multiaxial Test Frame

Figure 3.8 Photograph of multiaxial machine

Figure 3.9 Multiaxial machine and operator

Figure 3.10 Positioning of the transverse actuator

Figure 3.11 Main chamber

Figure 3.12 Four-post die set ured to high revolutions per minute during operation. As a result, one of the
MULTIAXIAL HIGH CYCLE FATIGUE TEST SYSTEM Priority is claimed for provisional application Ser. No. 60/273,134, filed Mar. 5, 2001. The provisional application is hereby incorporated by reference as though fully set forth.

The U.S. Government has rights in this invention under a development contract with the Air Force, Contract No. F33615-98-2812.

The invention relates to development of a multiaxial high cycle fatigue test system.

BACKGROUND OF THE INVENTION

Modern gas turbine engines need to maintain a balance between high performance, affordability, and design robustness. The rotating components of the turbine engine such as fan blades and turbine blades are subjected to high revolutions per minute during operation. As a result, one of the most common modes of failure in engine components is fatigue. This means that to improve the robustness of components, their fatigue behavior would have to be improved.

Component fatigue behavior can be improved, by improving either the material property or the component geometry or both. Material characteristics are typically studied by testing coupons. The effect of component geometry is lost in coupon tests. Finite element analysis can be used to simulate the actual component behavior to a certain extent. The best method would be to test the actual component by subjecting it to conditions similar to the operating conditions.

In a gas turbine engine, the fan blades and turbine blades rotate at high revolutions per minute during operation. The blades are subjected to a radial centrifugal force due to this rotation. Gas turbines have alternating stator and rotor blades. The stator blades guide the gas onto the rotor blades. As a rotor blade advances from one stator blade to the next, the gas pressure on the blade decreases and increases again. This results in the application of a cyclic load to the rotor blade. The blade also vibrates at its modal frequency under suitable conditions. These periodic loads result in a vibratory loading on the blade.

The following patents are of interest:

| Salberg et al | 4,802,365 | Feb. 7, 1989 |
| Owen et al | 6,023,980 | Feb. 15, 2000 |
| Wu et al | 4,875,375 | Oct. 24, 1989 |
| Meline et al | 4,607,531 | Aug. 26, 1986 |
| von Marinell et al | 3,696,512 | Oct. 10, 1972 |
| Rao | 4,748,854 | Jun. 7, 1988 |
| Detert et al | 3,603,143 | Sep. 7, 1971 |
| Ohya et al | 4,869,111 | Sep. 26, 1989 |

These patents relate to fatigue testing or axial and torsion testing. Sallberg et al have a multi-axial fatigue testing machine.

SUMMARY OF THE INVENTION

The invention relates to a multiaxial high cycle fatigue test system.

Vibratory loading causes high cycle fatigue failure in engine blades. To study and improve the fatigue life of gas turbine engine blades, or other test units such as components or material samples, a new test methodology has been proposed. According to this method, the blade or other test unit will be loaded multiaxially during testing, to simulate the actual operating conditions.

A multiaxial high cycle fatigue test system for testing bending, torsion, and tension of a test unit, comprises servo-hydraulic components, including a hydraulic service manifold, two small high frequency actuators along a first axis, and one large main actuator along a second axis. The large main actuator is used to apply a radial centrifugal force, and the two small actuators are used to apply vibratory loading; the two small side actuators being offset independently of each other, to enable the machine to apply both bending loads and torque to the test unit. The test unit is subjected to torsion loading when the traverse actuators move in phase, that is when both actuators move either in or out at the same time. The test unit is subjected to bending loading when the actuators move out-of-phase, that is one actuator moves in when the other moves out or vice-versa.

In the embodiment described in the detailed description, the test unit is a turbine blade. In general, the test unit may be any type of complete component, or a material sample, such as a portion of a component.

BRIEF DESCRIPTION OF THE DRAWING

FIG. 1.1 shows bending and torsion of a gas turbine blade;

FIG. 2.1 is a schematic of a biaxial loading machine;

FIG. 2.2 is a photograph of a biaxial loading machine;

FIG. 2.3 shows a blade gripping system for a biaxial machine;

FIG. 2.4 is a photograph of biaxial loading of a GE F110 fan blade;

FIG. 3.1 shows traverse loading in the multiaxial machine;

FIG. 3.2 shows torsion loading;

FIG. 3.3 shows bending loading;

FIG. 3.4 is a three-dimensional model of multiaxial loading mechanism;

FIG. 3.5 shows traverse loading of the blade;

FIG. 3.6 is a photograph of a multiaxial loading setup;

FIG. 3.7 shows a multiaxial test frame;

FIG. 3.8 is a photograph of a multiaxial machine;

FIG. 3.10 shows positioning of a traverse actuator;

FIG. 3.11 shows a main chamber; and

FIG. 3.12 shows a four-port die set.

Appendix A is a User's Manual which contains some computer screen drawings.

Appendix B comprises several pages of engineering drawings.

DETAILED DESCRIPTION 1.0 Introduction

Modern gas turbine engines need to maintain a balance between high performance, affordability, and design robustness. The rotating components of the turbine engine such as fan blades and turbine blades are subjected to high revolutions per minute during operation. As a result, one of the most common modes of failure in engine components is fatigue. This means that to improve the robustness of components, their fatigue behavior would have to be improved.

Component fatigue behavior can be improved, by improving either the material property or the component geometry or both. Material characteristics are typically studied by testing coupons. The effect of component geometry is lost in coupon tests. Finite element analysis can be used to simulate the actual component behavior to a certain extent. The best method would be to test the actual component by subjecting it to conditions similar to the operating conditions.

In a gas turbine engine, the fan blades and turbine blades rotate at high revolutions per minute during operation. The blades are subjected to a radial centrifugal force due to this rotation. Gas turbines have alternating stator and rotor blades. The stator blades guide the gas onto the rotor blades. As a rotor blade advances from one stator blade to the next, the gas pressure on the blade decreases and increases again. This results in the application of a cyclic load to the rotor blade. The blade also vibrates at its modal frequency under suitable conditions. These periodic loads result in a vibratory loading on the blade.

This vibratory loading causes high cycle fatigue failure in engine blades. To study and improve the fatigue life of gas turbine engine blades, a new test methodology has been proposed. According to this method, the blade will be loaded multiaxially during testing, to simulate the actual operating conditions. A prototype biaxial testing machine was proposed and demonstrated in Phase I of this program. The biaxial machine had two hydraulic actuators perpendicular to each other. This enabled the machine to apply both a radial load to simulate the centrifugal force, and a cyclic transverse load to simulate the vibratory loading. The single transverse actuator facilitated the application of bending loads.

Figure 11:
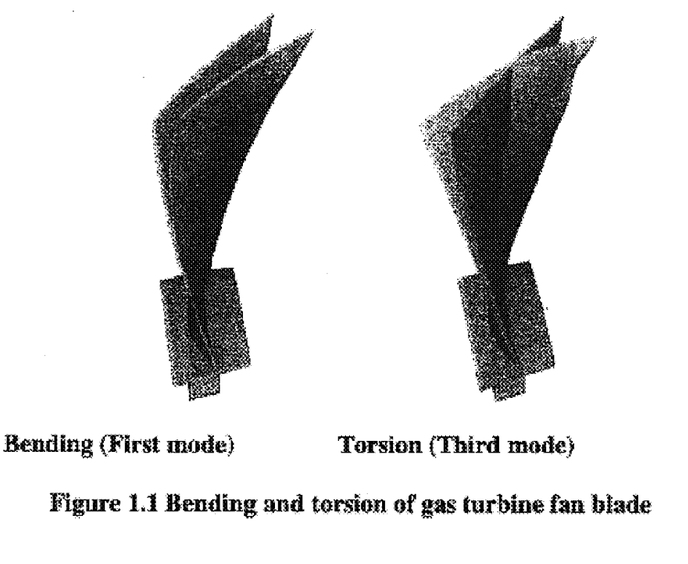

Vibration of turbine blades include both bending and torsion modes as shown in FIG. 1.1. The biaxial machine could not be used to apply torsion loads to the blade, as that required two actuators in the transverse direction. A multiaxial testing machine was proposed, designed and demonstrated in Phase II. The multiaxial machine had three hydraulic actuators, a large actuator along the vertical axis and two small actuators along the horizontal axis. The large actuator was used to apply the radial centrifugal force. The two small horizontal actuators were used to apply the vibratory loading. The two small side actuators can be offset independent of each other. This enabled the machine to apply not only bending loads but also torque to the blade. The application of bending and torsion loads to the blade is explained in detail in Section 3.1.

Figure 21:
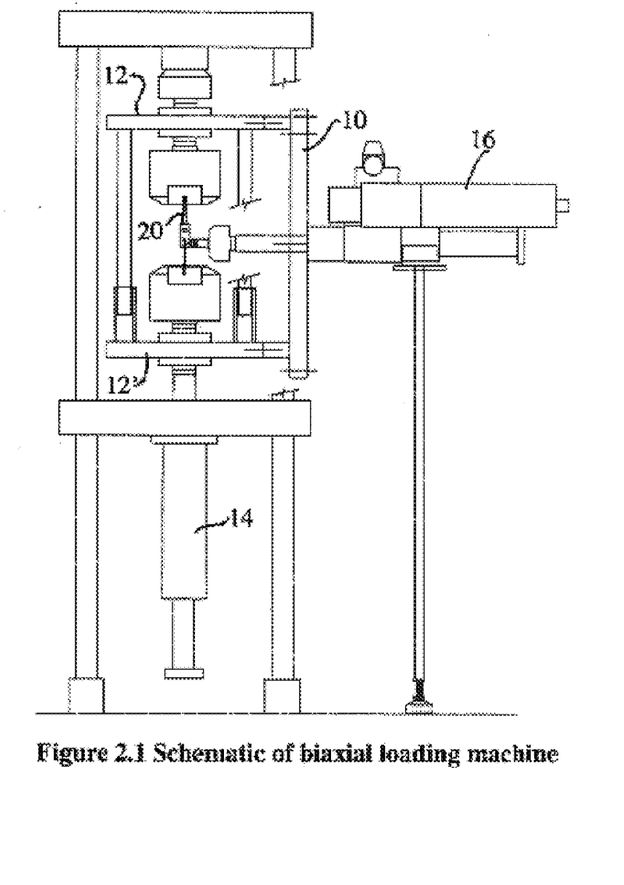
Figure 22:
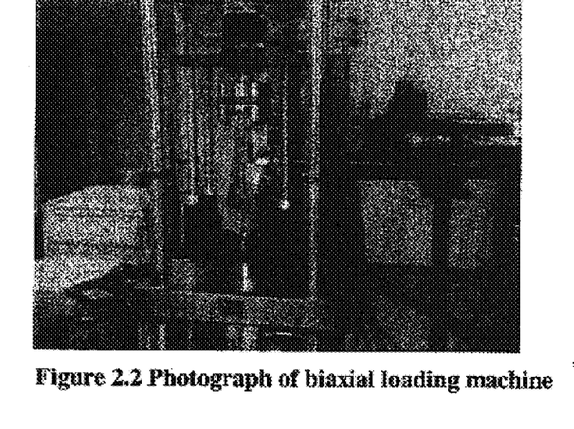

2.0 Prototype Test System with Biaxial Loading Capability 2.1 Design of a Biaxial Loading Test Frame In Phase I, an existing four-post test frame was modified to test a gas turbine engine fan blade under biaxial loading. A four-post die set was designed and fabricated. It was placed between the top and bottom platforms, and was mounted on the load train. A vertical plate 10 was mounted on the side of the die set 12–12', on which a second hydraulic actuator was mounted. FIG. 2.1 shows the schematic of the biaxial loading machine. FIG. 2.2 shows a photograph of the completed biaxial loading machine. The vertical actuator 14 was used to apply the steady radial load to simulate the actual centrifugal load on the blade. The horizontal actuator 16 was used to apply the fatigue loading to simulate the actual vibratory load. Both actuators were controlled by an Intelaken DDC4000 controller. The load and time data were collected in a computerized data acquisition system. Labtech Notebook was the data acquisition and analysis software used.

Figure 23:
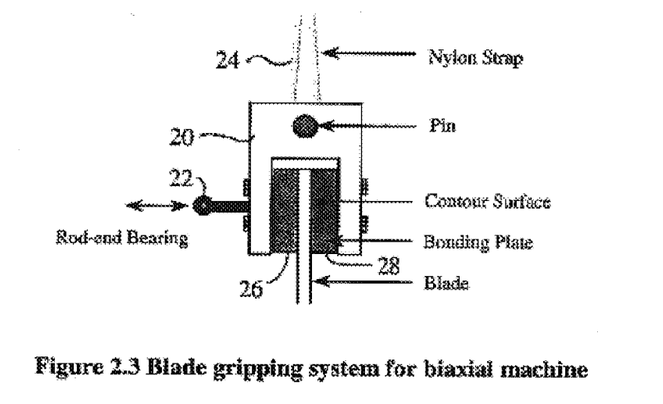

A gripping system 20 was designed and manufactured to apply the biaxial loading to the blade. A schematic of the gripping system is shown in FIG. 2.3. Transverse fatigue loading was applied to the blade through a rod end bearing 22 connection on the grip surface. The rod end bearing was connected to a clevis, which was in turn connected to the piston of the horizontal actuator 16. The rod-end bearing allows transverse fatigue loading to be applied to the test specimen and at the same time allows small rotation around the gripping. This extra degree of freedom will allow the test specimen to bend under transverse loading.

Figure 24:
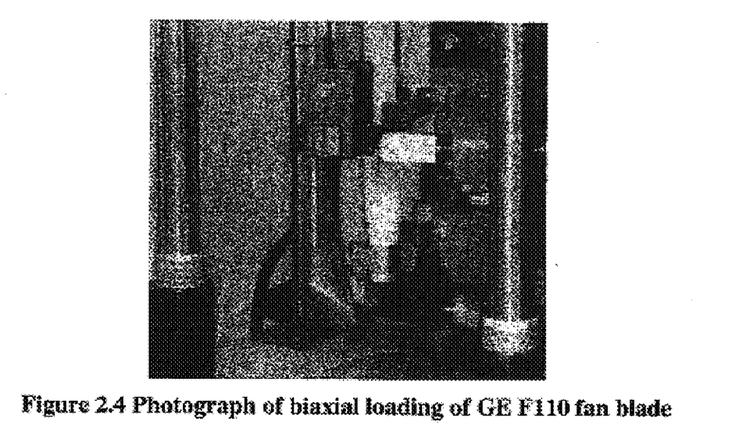

A nylon strap 24 was used to connect the fixture to the hydraulic grips. The nylon strap served as the flexible connection that prevented interference between the axial and lateral actuators. The gripping system had two bonding plates 26–28 whose internal contours conformed to the surface of the blade 30. A photograph of the complete setup is shown in FIG. 2.4.

A broach block was used to hold the turbine blade specimen in place. The broach block resembles a part of the turbine rotor disk. The dovetail of the blade slides into the block, and the blade was tightened against the block by two screws from underneath. The broach block was connected to the vertical actuator directly.

3.0 Design of the Multiaxial Loading Test System

Figure 37:
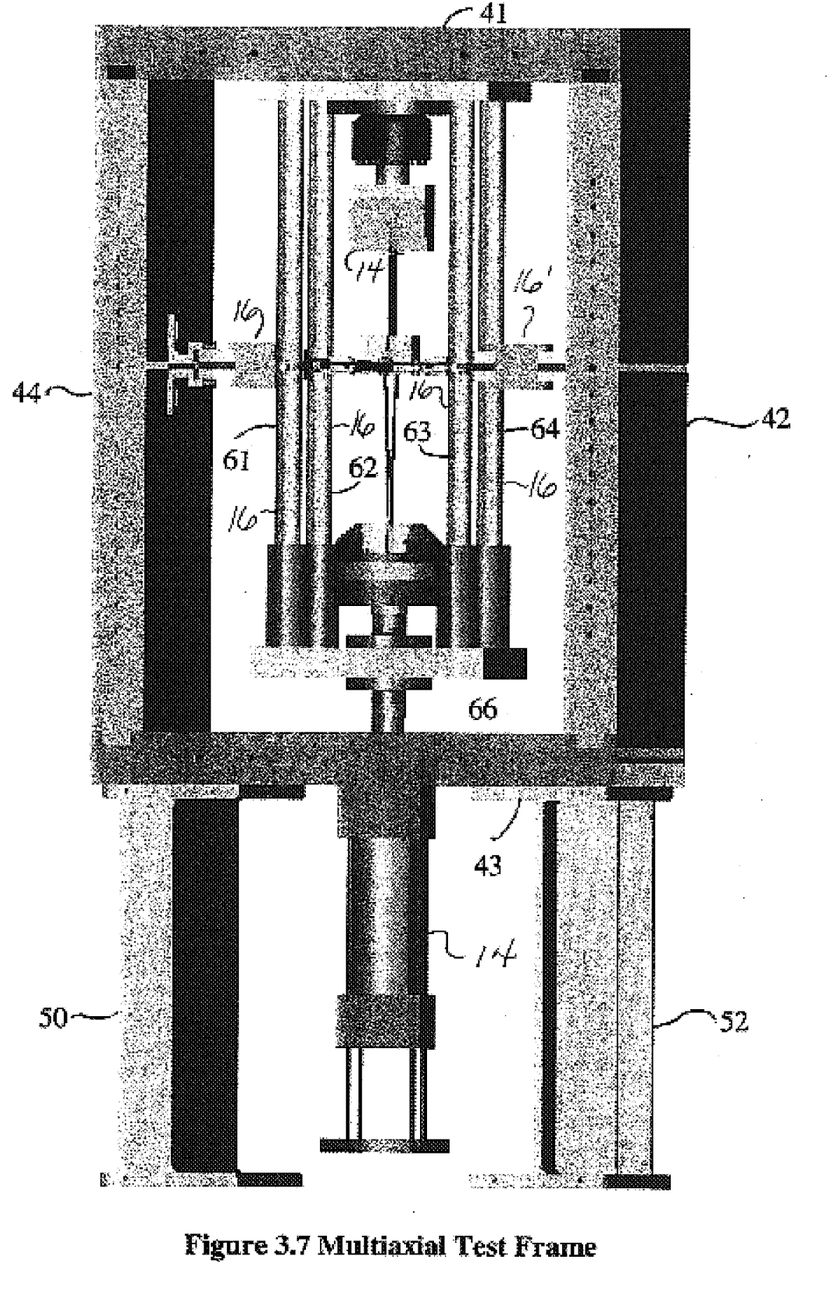
Figure 39:
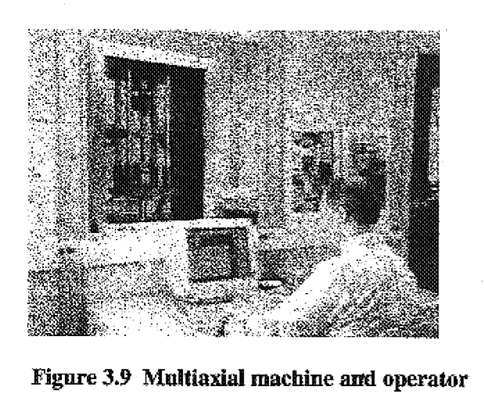

The multiaxial loading test system includes the following subsystems:

(1) Main test frame (FIG. 3.7), including an enclosed chamber with four side walls 41-42-43-44;

(2) Main test frame support, including two I-beam pedestals 50–52 reinforced by gussets;

(3) Auxiliary test frame support, including a four-post die set 61-62-63-64 and other mounting adaptors;

(4) Servo-hydraulic components, including hydraulic service manifold 66, two high frequency actuators 16–16' (1.1 kip, 400 Hz), and one main actuator 14 (11 kip);

(5) Multiaxial digital control and data acquisition system, including the control console and a computer workstation (FIG. 3.9) (See User's Manual).

The design features of the above subsystems will be discussed in the following paragraphs.

3.1 Concept of Bending and Torsion Loading

Figure 31:
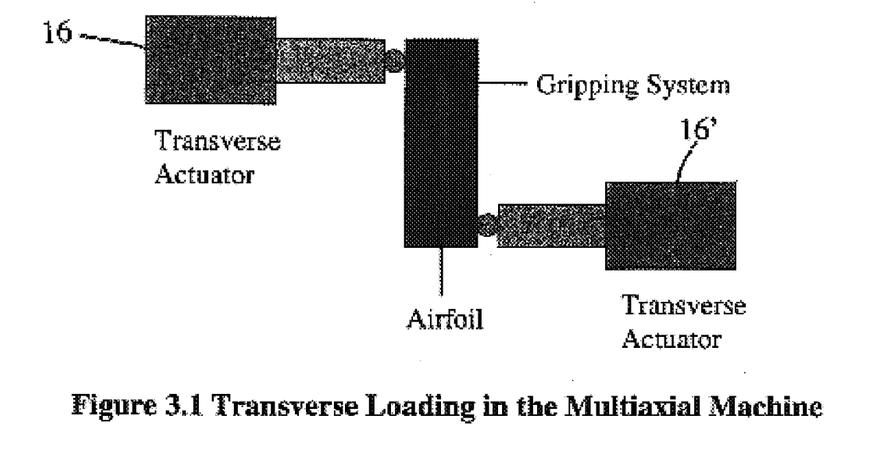

Since vibration of turbine engine blades under service conditions include bending and torsion modes, two actuators have been designed into the test system to simulate the bending and torsional vibration loading. A schematic of the top view of the transverse actuators in relation to the blade is shown in FIG. 3.1.

Figure 32:
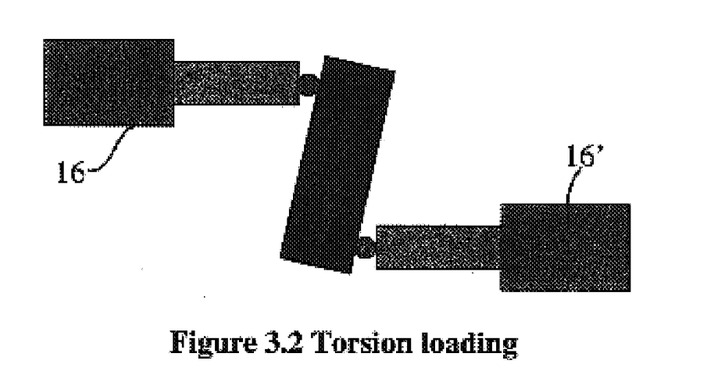
Figure 33:
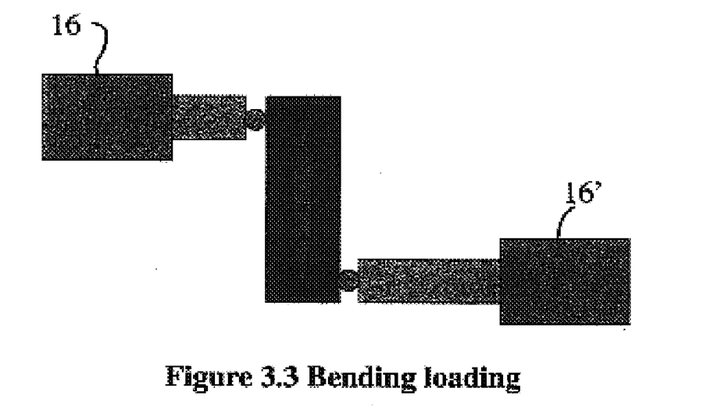

The blade is subjected to torsion loading when the transverse actuators move in-phase, that is when both actuators move either in or out at the same time. FIG. 3.2 shows a schematic of the torsion loading. The blade is subjected to bending loading when the actuators move out of phase, that is one actuator moves in when the other moves out or vice-versa. FIG. 3.3 shows a schematic of the bending loading.

3.2 Design of the Gripping System

Figure 34:
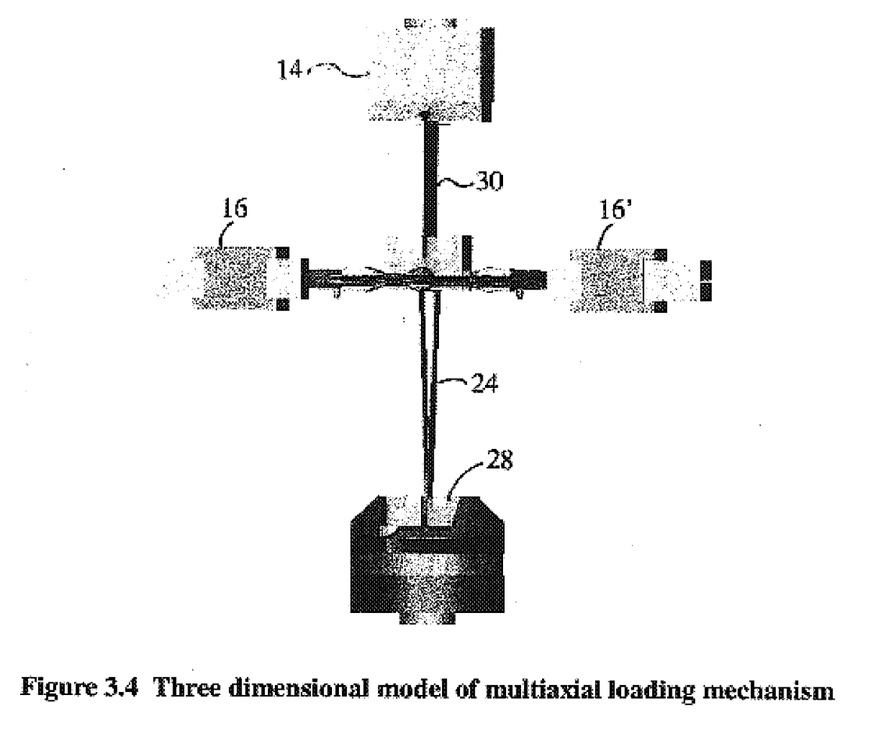

A new gripping system was designed and manufactured to apply the multiaxial loading to the blade. FIG. 3.4 shows the three-dimensional model of the gripping and loading system developed during the design stage of phase II. The broach block used in phase-I was used after some modifications. The dovetail of the blade slides into the dovetail of the broach block, and the blade is tightened against the block by two screws from underneath. To access these two screws, the broach block has to be removed from the machine every time the blade has to be removed. In phase-I, the broach block was connected to the moving die plate by a threaded rod. So the broach block had to be setup again each time, as its position moved every time it was removed from the machine.

An adapter was added to the base of the broach block in phase-II. The adapter was connected to the stationary die plate by a threaded rod. The broach block was located on the adapter plate by two dowel pins, and it was attached to the adapter plate by four bolts. This facilitated the easy assembly and removal of the broach block and the blade for each test. The dowel pins ensured that the broach block is returned to the same position as before it was removed from the machine. This eliminates the need for setting up the broach block between tests on same or similar blades.

The strap 24 is gripped by a hydraulic wedge grip 28. In phase-I, the hydraulic grip was mounted on the top (fixed) die plate, while the broach block and specimen were mounted on the bottom (movable) die plate attached to the vertical actuator 14. As a result, the position of the specimen relative to the transverse actuator changed whenever the vertical actuator moved and whenever the hydraulic power was switched off. In the new multiaxial test frame, the hydraulic grip is mounted on the bottom (movable) die plate attached to the vertical actuator. The broach block and the specimen are mounted on the top (fixed) die plate. This ensures that the relative distance between the specimen and the transverse actuators remains undisturbed by the movements of the vertical actuator. This also enables quick change over from one test to another on same or similar blades, by eliminating changes in the critical locating dimensions.

Figure 35:
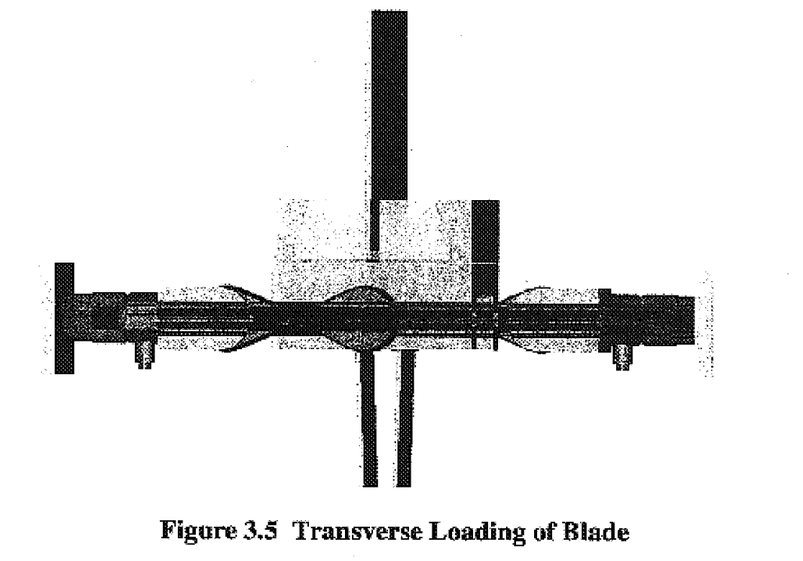
Figure 36:
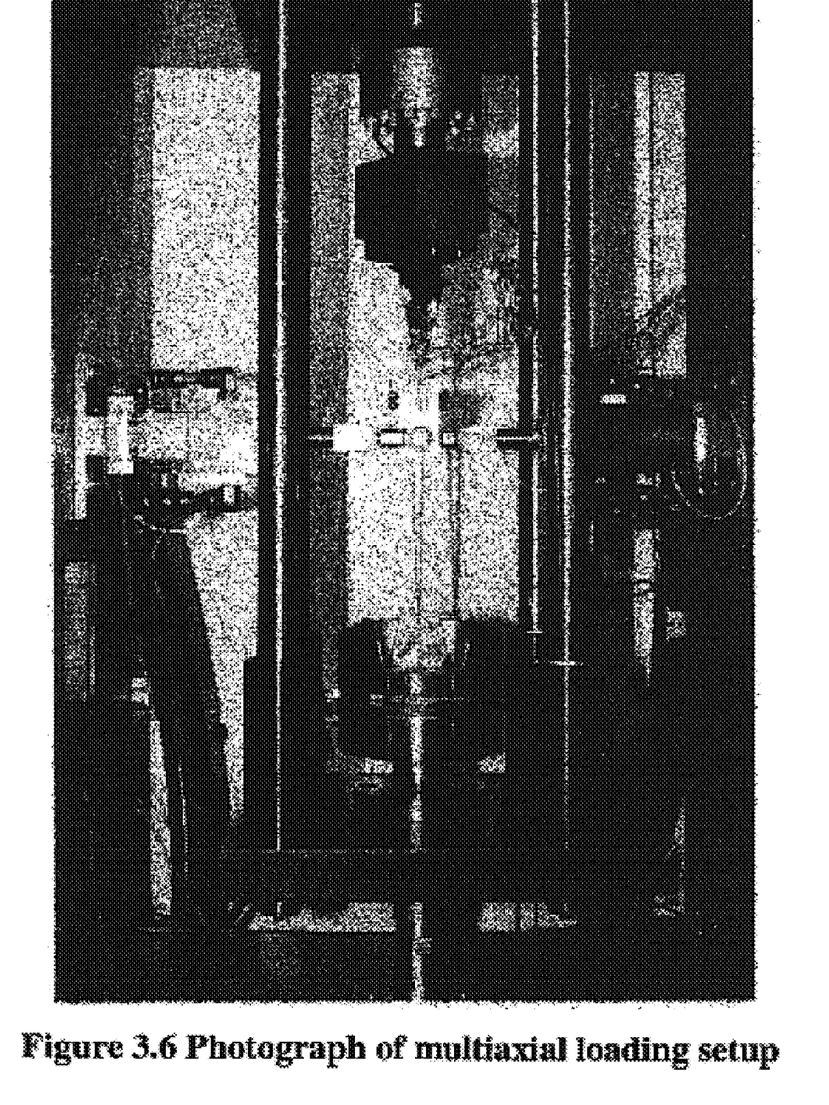

A load cell of 2000 lb capacity supplied by Sensotec is mounted on the piston rod of each transverse actuator using an adapter. A clevis is attached to the load cell. The clevis is connected to the grip pin using two rod end bearings. The grip pin extends from one end of the grip to the other end. When the piston rod of a lateral actuator moves forward, it pushes one end of the grip pin forward via the clevis and the rod end bearings. This results in the application of a force to the specimen in the direction of the actuator movement. The rod end bearings and the clevis joints allow movement of the grip in the vertical direction to a certain extent. A three-dimensional model of the transverse loading mechanism is shown in FIG. 3.5. A photograph of the GE F110 gas turbine engine fan blade subjected to multiaxial loading using the gripping system is shown in FIG. 3.6.

3.3 Hydraulic Components and Control System

The hydraulic control system and the actuators were procured from Instron Schenk Testing Systems. Labtronic 8800 multi-axis digital control console manufactured by Instron is used to control all the three actuators. It monitors the load and displacement conditions while performing high speed data acquisition. Labtronic 8800 has multi-station capability. The Labtronic 8800 control console is connected to a personal computer running Windows NT. A software called RS Console is used for interacting with the Labtronic 8800 control console. RS Console can be used for set up, waveform generation and setting of limits. It uses a wizard to provide simple easy to use instructions for complex operations. The software also includes multiple live displays for digital readout of data. RS Console has function generators that can be interlocked with phase control. This enables the maintenance of phase relations between the actuators during cyclic loading.

The two lateral actuators are of type PLF7D supplied by Instron. Each actuator has a capacity of 1,100 lb (5.2 kN) and 20 mm stroke. These actuators can apply high frequency loading up to 400 Hz. Standard fatigue rated actuators using high pressure rod seals experience a banding problem resulting in early failure. When the dynamic stroke is too small to carry fresh oil under the seals, the oil film breaks down and results in damage to the rod. The PLF7D servo hydraulic actuators are designed, built and optimized for high frequency operation. Hydrostatic bearings and laminar high pressure seals allow sustained high frequency, short stroke operation. The actuator does not have any elastomer seals in contact with the piston rod during operation. The single rod seal that prevents external leakage when turned off is retracted from the rod when operating. A suction pump is used to scavenge the leakage oil during operation.

The vertical actuator is a labyrinth bearing pedestal base actuator supplied by Instron. The actuator has a dynamic force rating of +/−11,000 lb (50 kN) and +/−50 mm stroke. The rod diameter is 63.5 mm and the actuator stall force is 63 kN. The load in the vertical direction is measured by a dynamic load cell of 11,000 lb (50 kN) capacity.

All three actuators are connected to servo valves. The servo valves are connected to a hydraulic service manifold (HSM). The hydraulic service manifold is in turn connected to the hydraulic power supply. Accumulators are provided in the hydraulic service manifold to enable high frequency operation of the actuators.

The procedure for operating the test frame using the RS Console software and the Labtronic 8800 controller are described elaborately in Appendix A.

3.4 Design of the Multiaxial Test Frame

The major structural components of the multiaxial test frame are a main chamber with four side walls, two I-beam pedestals and a four-post die set. FIG. 3.7 shows a three-dimensional model of the multiaxial test frame.

Figure 38:
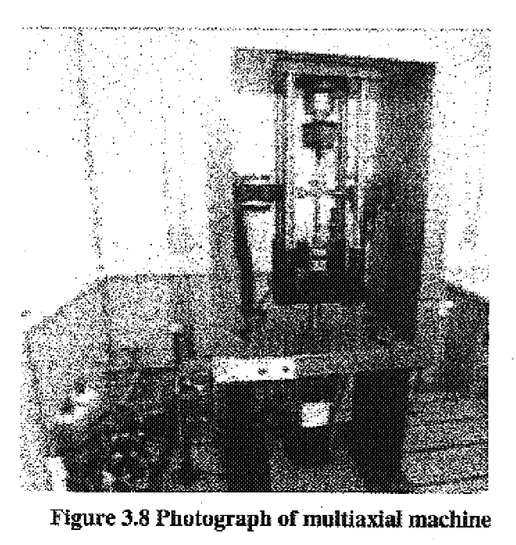

A photograph of the complete multiaxial test frame is shown in FIG. 3.8. The test frame and the hydraulic service manifold are located inside an enclosed test chamber as shown in FIG. 3.9. The control system and the personal computer that acts as the interface with the user are located outside the chamber. This isolation of the test frame helps to reduce the noise pollution of the surroundings. The I-beam pedestals of the machine are bolted to a metallic test bed using T-bolts. This prevents the machine from moving due to vibrations during high frequency tests. The I-beams are separated from the test bed by neoprene pads. The neoprene pads reduce the transfer of vibrations from the test frame to the test bed.

Figure 310:
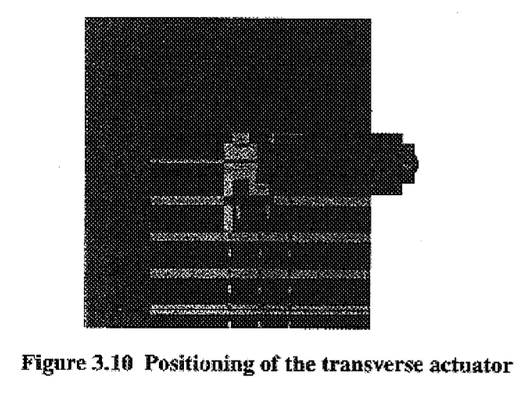

The side frame walls of the test frame have three rows of threaded holes. The actuator fixtures are bolted to the side frame walls using these holes. This is shown in FIG. 3.10. The rows of holes allow the actuator fixtures to be moved and positioned both in the vertical and horizontal directions. This enables the positioning of the lateral actuators at different points with respect to the specimen. The base of the lateral actuator slides inside a slot in the actuator fixture and the actuator is bolted to the fixture. This allows the actuator to be moved along the slot to a certain extent for quick adjustments. The actuator fixture has slots that are used to bolt it to the side frame wall. These slots allow the fixture to be moved in the vertical direction to a certain extent for quick adjustments.

Figure 311:
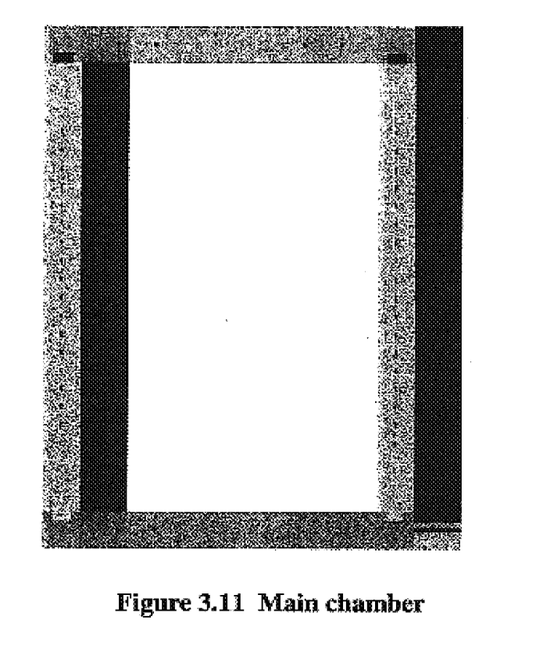

The main chamber of the multiaxial test frame consists of four frame walls that are 4 inch thick. The construction of the main chamber is shown in FIG. 3.11. The top and the bottom frame walls have machined grooves. The side frame walls have matching machined projections that rest in these grooves. This reduces the movement of the side frame walls due to the forces from the transverse actuators. This also reduces the transfer of the transverse forces to the bolts holding the walls together. A row of threaded holes is provided on the front and back sides of the frame walls to facilitate easy attachment of ancillary equipment such as measuring devices and cameras.

Figure 312:
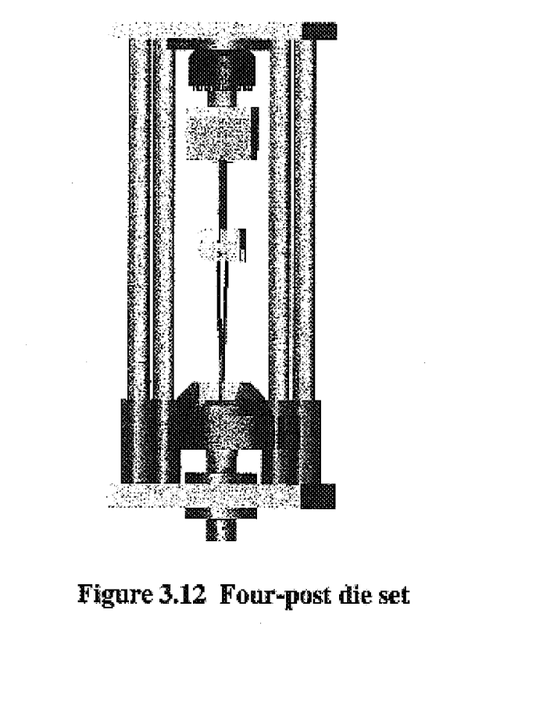

A four-post die set is used in the vertical load train. The four-post die set is used to minimize the effects of the lateral loading on the piston rod of the vertical actuator. The top plate of the die set is bolted to the top frame wall. The load cell that measures the load in the vertical axis is bolted to the top plate. The broach block is attached to the broach block adapter plate, which in turn is attached to the load cell. The hydraulic grip used to grip the strap is mounted to the bottom die plate using a threaded rod. The bottom die plate is attached to the piston rod of the vertical actuator. When the piston rod of the vertical actuator is moved downwards, the strap is pulled resulting in a vertical load on the specimen. The four-post die set is shown in FIG. 3.12.

The actual dimensions of the manufactured parts and the materials used to manufacture them are shown in the detailed drawings attached as Appendix B.

What is claimed is:

1. A multiaxial high cycle fatigue test system for testing bending, torsion, and tension of a gas turbine fan blade, comprising the following subsystems:
   (1) a main test frame support, including an enclosed chamber with four side walls:
   (2) a main test frame support, including two I-beam pedestals reinforced by gussets;
   (3) an auxiliary test frame support, including a four-post die set;
   (4) servo-hydraulic components, including a hydraulic service manifold two high frequency actuators along a horizontal axis, and one large main actuator along a vertical axis;
   (5) a multiaxial digital control and data acquisition system, including a control console and a computer work station;
      wherein the large vertical actuator is used to apply a radial centrifugal force, and the two small horizontal actuators are used to apply vibratory loading; the two small side actuators being offset independently of each other, to enable the machine to apply both bending loads and torque to the blade;
      the blade being subjected to torsion loading when the traverse actuators move in phase, that is when both actuators move either in or out at the same time, and the blade being subjected to bending loading when the actuators move out-of-phase, that is one actuator moves in when the other moves out or vice-versa.

2. A multiaxial high cycle fatigue test system for testing bending, torsion, and tension of a gas turbine fan blade, comprising the following subsystems:
   (1) a main test frame support, including an enclosed chamber with four side walls:
   (2) a main test frame support, including two I-beam pedestals reinforced by gussets;
   (3) an auxiliary test frame support, including a four-post die set;
   (4) servo-hydraulic components, including a hydraulic service manifold two
      small high frequency actuators along a horizontal axis, and one large main actuator along a vertical axis;
   (5) a multiaxial digital control and data acquisition system, including a control console and a computer work station;
      wherein the large vertical actuator is used to apply a radial centrifugal force, and the two small horizontal actuators are used to apply vibratory loading; the two small side actuators being offset independently of each other, to enable the machine to apply both bending loads and torque to the blade;
      the blade being subjected to torsion loading when the traverse actuators move in phase, that is when both actuators move either in or out at the same time, and the blade being subjected to bending loading when the actuators move out-of-phase, that is one actuator moves in when the other moves out or vice-versa;
   further including a gripping system to apply the multiaxial loading to the blade;
   a broach block, wherein a dovetail of the blade slides into a dovetail of the broach block, and the blade is tightened against the block by two screws from underneath;
   an adapter added to the base of the broach block, the adapter being connected to the stationary die plate by a threaded rod, the broach block being located on the adapter plate by two dowel pins, and attached to the adapter plate by four bolts, which facilitates the easy assembly and removal of the broach block and the blade for each test, wherein the dowel pins ensure that the broach block is returned to the same position as before it was removed from the machine, which eliminates the need for setting up the broach block between tests on same or similar blades;
   a strap which is gripped by a hydraulic wedge grip, the hydraulic grip being mounted on the bottom (movable) die plate attached to the vertical actuator, the broach block and the specimen are mounted on the top (fixed) die plate, which ensures that the relative distance between the specimen and the transverse actuators remains undisturbed by the movements of the vertical actuator, and which also enables quick change over from one test to another on same or similar blades, by eliminating changes in the critical locating dimensions.

3. A multiaxial high cycle fatigue test system according to claim 2, wherein the two high frequency actuators provide 1.1 kip in the range of 0–400 Hz, and the main actuator operates at 11 kip;
   wherein the system further includes a load cell of 2000 pound capacity mounted on the piston rod of each transverse actuator using an adapter, a clevis being attached to the load cell, the clevis being connected to the grip pin using two rod end bearings, wherein the grip pin extends from one end of the grip to the other end, wherein when the piston rod of a lateral actuator moves forward, it pushes one end of the grip pin forward via the clevis and the rod end bearings, which results in the application of a force to the specimen in the direction of the actuator movement, and wherein the rod end bearings and the clevis joints allow movement of the grip in the vertical direction to a certain extent.

4. A multiaxial high cycle fatigue test system for testing bending, torsion, and tension of a test unit, comprising:
   servo-hydraulic components, including a hydraulic service manifold, two small high frequency actuators along a first axis, and one large main actuator along a second axis;
   wherein the large main actuator is used to apply a radial centrifugal force, and the two small actuators are used to apply vibratory loading; the two small side actuators being offset independently of each other, to enable the machine to apply both bending loads and torque to the test unit;
   the test unit being subjected to torsion loading when the traverse actuators move in phase, that is when both actuators move either in or out at the same time, and the test unit being subjected to bending loading when the actuators move out-of-phase, that is one actuator moves in when the other moves out or vice-versa, further including a gripping system to apply the multiaxial loading to the test unit;

a broach block having an adapter connected to a stationary die plate to facilitate easy assembly and removal of the broach block and the test unit for each test, wherein dowel pins ensure that the broach block is returned to the same position as before it was removed from the machine, which eliminates the need for setting up the broach block between tests on same or similar blades.

5. A multiaxial high cycle fatigue test system according to claim 4, wherein the test unit is a component or a material sample.

6. A multiaxial high cycle fatigue test system according to claim 4, further including a strap which is gripped by a hydraulic wedge grip, the hydraulic grip being mounted on the bottom (movable) die plate attached to the vertical actuator, wherein the broach block and the specimen are mounted on the top (fixed) die plate, which ensures that the relative distance between the specimen and the transverse actuators remains undisturbed by the movements of the vertical actuator, and which also enables quick change over from one test to another on same or similar blades, by eliminating changes in the critical locating dimensions.

7. A method of testing a test unit for bending, torsion, and tension, comprising:

using servo-hydraulic components, including a hydraulic service manifold, two small high frequency actuators along a first axis, and one large main actuator along a second axis;

using the large main actuator to apply a radial centrifugal force, and using the two small actuators are to apply vibratory loading; the two small side actuators being offset independently of each other, to enable the machine to apply both bending loads and torque to the test unit;

subjecting the test unit to torsion loading when the traverse actuators move in phase, that is when both actuators move either in or out at the same time, and subjecting the test unit to bending loading when the actuators move out-of-phase, that is one actuator moves in when the other moves out or vice-versa.

further including using a gripping system to apply the multiaxial loading to the test unit;

using a broach block having an adapter connected to a stationary die plate to facilitate easy assembly and removal of the broach block and the test unit for each test, wherein dowel pins ensure that the broach block is returned to the same position as before it was removed from the machine, which eliminates the need for setting up the broach block between tests on same or similar blades.

8. A method according to claim 7, wherein the test unit is turbine blade.

* * * * *